United States Patent
Kimzey et al.

(10) Patent No.: US 11,111,268 B2
(45) Date of Patent: Sep. 7, 2021

(54) USE OF QUATERNARY AND TERTIARY AMMONIUM CATIONS TO DENATURE PROTEINS

(71) Applicant: ProZyme, Inc., Hayward, CA (US)

(72) Inventors: Michael J. Kimzey, Laguna Hills, CA (US); Francis T. Haxo, San Francisco, CA (US); Vaishali Sharma, Union City, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 200 days.

(21) Appl. No.: 16/323,247

(22) PCT Filed: Aug. 17, 2017

(86) PCT No.: PCT/US2017/047455
§ 371 (c)(1),
(2) Date: Feb. 4, 2019

(87) PCT Pub. No.: WO2018/035386
PCT Pub. Date: Feb. 22, 2018

(65) Prior Publication Data
US 2019/0169230 A1  Jun. 6, 2019

Related U.S. Application Data

(60) Provisional application No. 62/376,342, filed on Aug. 17, 2016.

(51) Int. Cl.
| | |
|---|---|
| *A61K 38/39* | (2006.01) |
| *C07K 1/113* | (2006.01) |
| *C11D 1/62* | (2006.01) |
| *C11D 17/00* | (2006.01) |

(52) U.S. Cl.
CPC ............ *C07K 1/1136* (2013.01); *C07K 1/113* (2013.01); *C11D 1/62* (2013.01); *C11D 17/00* (2013.01)

(58) Field of Classification Search
None
See application file for complete search history.

(56) References Cited

U.S. PATENT DOCUMENTS

| | | |
|---|---|---|
| 7,250,269 B2 | 7/2007 | Kouzuma |
| 8,198,063 B1 | 6/2012 | Baginski |

FOREIGN PATENT DOCUMENTS

| | | |
|---|---|---|
| EP | 1362925 A1 | 11/2003 |
| WO | WO2008/128225 A1 | 10/2008 |
| WO | WO 2013/025527 A1 | 2/2013 |

OTHER PUBLICATIONS

EPO Extended European Search Report for EP Application 17842158.2, dated Mar. 5, 2020.
Lee, A., et al., Denaturation of Proteins by SDS and Tetraalkylammonium Dodecyl Sulfates, Langmuir, 2011, pp. 11560-574, v. 27(18).
Lee et al., "Denaturation of Proteins by SDS and Tetraalkylammonium Dodecyl Sulfates," Langmuir, Aug. 11, 2011, pp. 11560574, vol. 27.
Moosavi-Movahedi, et al., "Thermodynamics of denaturation of horseradish peroxidase with [SDS] . . . ," Colloids and Surfaces B: Biointerfaces. Jul. 31, 1997, pp. 123-130, vol. 9.
Tao et al., "A Novel Method for Relative Quantitation of N-Glycanse by Isotopic Labeling Using 18O Water," J Biomolecular Techniques, Dec. 2014, pp. 111-117, vol. 25.
Young, L., International Search Report, PCT/US2017/047455, dated Nov. 6, 2017.
Young, L., Written Opinion, PCT/US2017/047455, dated Nov. 6, 2017.

*Primary Examiner* — Jeanette M Lieb
(74) *Attorney, Agent, or Firm* — Laurence J. Hyman; Hyman IP Law

(57) ABSTRACT

Ammonium cation detergents comprising a quaternary or tertiary ammonium cation can be used as detergents to denature proteins and are particularly useful in denaturing glycoproteins or glycopeptides prior to enzymatic deglycosylation. Ammonium cation detergents with sulfate or sulfonate anions are particularly useful.

50 Claims, 2 Drawing Sheets

| Glycoprotein | Sodium dodecyl sulfate | Tetramethylammonium lauryl sulfate |
|---|---|---|
| hIgG | 76.7% | 100% |
| ZALTRAP® | 88.7% | 100% |
| Cetuximab | 109% | 100% |
| hIgA | 99.4% | 100% |
| Nist mAB | 96.8% | 100% |
| RITUXAN® | 96.6% | 100% |
| ENBREL® | 88.0% | 100% |
| ORENCIA® | 85.5% | 100% |
| hIgM | 82.0% | 100% |

FIG. 1

USE OF QUATERNARY AND TERTIARY AMMONIUM CATIONS TO DENATURE PROTEINS

CROSS-REFERENCE TO RELATED APPLICATIONS

This application is a national stage application under 35 U.S.C. § 371 of International Application No. PCT/US2017/047455, filed Aug. 17, 2017, which is hereby incorporated by reference. This application claims the benefit of priority to U.S. Provisional Patent Application No. 62/376,342, filed Aug. 17, 2016, the contents of which are incorporated herein by reference for all purposes.

STATEMENT OF FEDERAL FUNDING

Not applicable.

BACKGROUND OF THE INVENTION

This invention relates to the field of analysis of glycosylation of glycoproteins.

Many of the proteins produced by eukaryotic cells are modified after translation by the addition of covalently-linked, linear or branched chains of carbohydrates. These protein-carbohydrate conjugates are referred to as glycoproteins; the point at which the carbohydrate is attached is referred to as a glycosylation site. Attached polysaccharides or oligosaccharides are referred to as glycans. A wide range of glycans are found on the different glycosylation sites of particular glycoproteins. The particular pattern of glycans on a particular glycoprotein is determined by the specific cell line that produced the protein and the conditions under which the cells were grown.

Since the glycans conjugated to a protein can affect characteristics critical to its function, including pharmacokinetics, stability, bioactivity, or immunogenicity, it is important in many uses to determine which glycans are present. Thus, the ability to remove some or all of the glycans from a protein and to analyze the glycans or the protein, or both, to determine their composition or compositions is useful for determining whether a protein will have a desired effect. For example, the Food and Drug Administration requires characterization of carbohydrates attached to biologics (such as therapeutic glycoproteins and vaccines) to show composition of matter and consistency of manufacture, resulting in a need for extensive characterization of the product. Analysis of the profile of the released carbohydrates is also important for quality control in the production of recombinant proteins, in which a change in carbohydrate profile may indicate stress in the system, signaling conditions that may require a commercial-scale fermenter of expensive protein to be discarded.

The techniques used to analyze glycans are complex, cumbersome and often time-consuming. The glycans must be released or removed from the protein, a process known as "deglycosylation", before analysis can be performed. Further, the samples to be analyzed typically include cell lysates, cell culture supernatants, and clinical plasma or serum samples, which may contain a multitude of glycoproteins in addition to the one of interest. Thus, companies wishing to obtain analysis of the carbohydrates attached to a particular glycoprotein, such as an antibody intended for therapeutic use in humans, often have first to perform a number of steps to isolate the target glycoprotein from others in the raw sample.

Only a subset of proteins can be deglycosylated under native, or non-denaturing, conditions, in which the protein is simply mixed with an enzyme that will release from the protein the glycans conjugated to the protein. These methods have the advantage of mild conditions and simple clean up, but often result in incomplete release of glycans. For most proteins being deglycosylated by enzymatic digestion, however, the secondary and tertiary structures of the proteins do not permit access of the enzyme to the carbohydrates unless the protein is first denatured to alter those structures. Traditional protocols for denaturing involve the use of detergents and reducing agents, and an overnight incubation. For example, these protocols typically add to the glycoprotein a reducing agent such as beta-mercaptoethanol, an anionic detergent, such as sodium dodecyl (lauryl) sulfate, a non-ionic detergent, such as octylphenolpoly(ethyleneglycolether), and a deglycosylating enzyme, and incubating the resulting mixture for 16 hours at 37° C. Once the protein is deglycosylated, the glycans are removed and, usually, are labeled. These protocols are effective and largely independent of the protein (that is, they can be used on most proteins), but are harsh, typically use detergents which must be removed before some analytical processes can be conducted, and can have a number of clean-up steps.

In commercial cell culture settings, the length of sample processing, typically at least a day, when these standard deglycosylation methods are used reduces the possibility of using carbohydrate analysis as a marker for rapid, in-process analysis and as a tool for control of process variables, such as stress during the cell culture process. The use of detergents adds steps and time since any detergent remaining with the released glycans can interfere with the results of mass spectrometry or other techniques used to analyze the carbohydrate profile Release of the glycans from the glycoprotein is typically achieved by one of two methods, chemical release or enzymatic digestion. Most of the available methods for chemical release result in the destruction of the protein backbone of the glycoprotein, and are therefore unsuitable when analysis of the protein component of the glycoprotein is desired. Enzymatic digestion usually occurs under milder conditions and leaves the protein component intact. It is therefore preferable in many analytical situations. Enzymatic digestion is particularly useful for removing N-glycans (glycans linked to the protein through amide groups of asparagine residues), which can be released from glycoproteins by enzymatic cleavage using the exemplar enzyme PNGase F (Peptide-N4-(acetyl-β-glucosaminyl)-asparagine amidase, EC 3.5.1.52) or endoglycosidases such as endo-alpha-N-acetyl-galactosaminidase, Endoglycosidase F1, Endoglycosidase F2, Endoglycosidase F3, or Endoglycosidase H. The glycans are then typically treated to label their free-reducing terminus with a fluorescent dye, excess label in removed, and the labeled glycans analyzed by methods such as high performance liquid chromatography (HPLC), capillary electrophoresis (CE), or carbohydrate gel electrophoresis. The protein component can be analyzed by any of various techniques, including mass spectrometry (MS). Both enzymatic digestion and chemical deglycosylation procedures encompass multiple steps, extended incubation times, and clean-up steps prior to analysis of the released glycans.

More recently, various protocols have been developed which reduce the time needed for deglycosylation compared to traditional protocols. In 2010, Agilent Technologies announced the introduction of a so-called "mAb-Glyco Chip" for deglycosylation and analysis of monoclonal antibodies, in which a deglycosylation enzyme is immobilized in a thin capillary in which the monoclonal antibodies of interest are flowed. Agilent's product materials stated that the system allows deglycosylation of the monoclonal antibodies in four minutes. In another example, U.S. Patent Publication No. 20130171658 describes methods of releasing glycans from a target glycoprotein in a biological sample in which the biological sample is added to a solid support comprising an affinity ligand immobilized in a packed bed, on a monolith, or on a membrane, binding the target glycoprotein, washing away any unbound glycoprotein, and then contacting the bound target with a deglycosylation enzyme to release glycans from the glycoprotein. This protocol permits rapid isolation and deglycosylation of a target glycoprotein even if other glycoproteins in the sample are not known. These protocols are based, in part, on improving the kinetics of the enzymatic deglycosylation by placing the glycoprotein into close proximity to an immobilized enzyme, as compared to traditional protocols in which both the enzyme and the glycoprotein are in solution and react by solution-phase kinetics.

Reagent and device manufacturers have also tried to find reagents which reduce the number of steps or time to complete an analytical workflow, U.S. Pat. No. 7,229,539 discloses degradable surfactants which do not need to be removed following the deglycosylation reaction. According to the patent, once deglycosylation has taken place, the surfactant is degraded by adding an acid to the medium and the resulting products are compatible with MS.

There remains a need for additional methods of deglycosylation that can be performed rapidly, that reduce handling and clean up steps, and that are suitable for use with multiple analytic methods, particularly with mass spectrometry. Surprisingly, the present invention meets these and other needs.

BRIEF SUMMARY OF THE INVENTION

In some embodiments, the invention provides methods of denaturing a glycoprotein or glycopeptide of interest in vitro, comprising incubating the glycoprotein or glycopeptide in vitro with a solution comprising an effective amount of an ammonium cation sulfate or sulfonate detergent comprising (a) an aliphatic chain of 8-24 carbons, (b) a sulfate or sulfonate anion and (c) a tertiary or quaternary ammonium cation, wherein said aliphatic chain is covalently attached to said anion, for a time T to denature said glycoprotein or glycopeptide, thereby denaturing said glycoprotein or glycopeptide. In some embodiments, the anion is a sulfate anion. In some embodiments, the anion is a sulfonate anion. In some embodiments, the chain of 8-24 carbons is saturated. In some embodiments, the aliphatic chain is of 8-15 carbons. In some embodiments, the aliphatic chain is of 8-13 carbons. In some embodiments, the aliphatic chain is 12 carbons. In some embodiments, the aliphatic chain is saturated. In some embodiments, the aliphatic chain is in a ring configuration. In some embodiments, the sulfate or sulfonate anion is covalently attached to said aliphatic chain by being attached to a benzyl which is attached to the aliphatic chain. In some embodiments, the cation is a quaternary ammonium cation. In some embodiments, the quaternary ammonium cation is selected from the group consisting of:

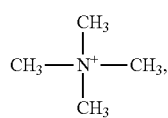

Cation 1

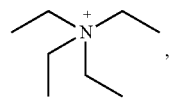

Cation 2

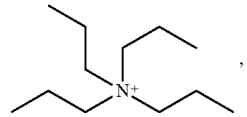

Cation 3

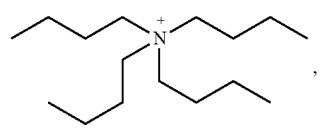

Cation 4

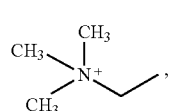

Cation 5

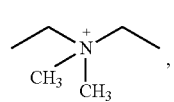

Cation 6

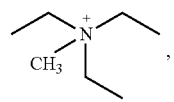

Cation 7

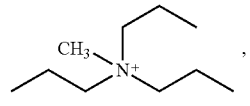

Cation 8

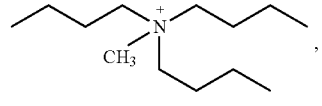

Cation 9

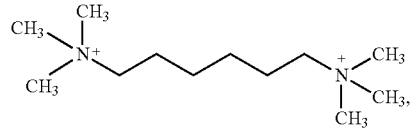

Cation 10

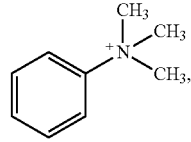

Cation 11

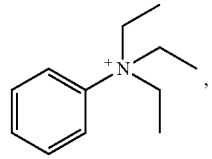

Cation 12

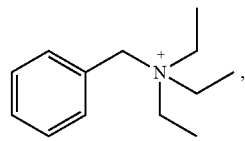

Cation 13

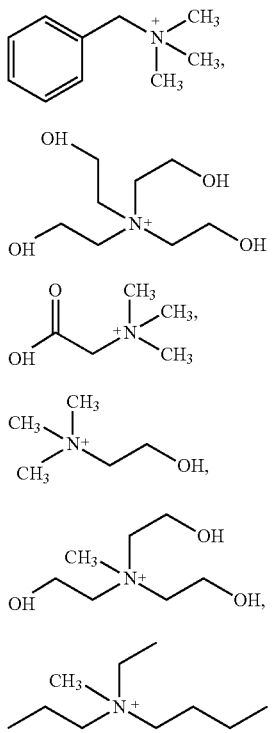

In some embodiments, the quaternary ammonium cation is a tetramethylammonium cation. In some embodiments, the quaternary ammonium cation is a tetrabutyl, a tetraethyl, or a tetrapropyl ammonium cation. In some embodiments, the ammonium cation detergent is tetramethyl dodecyl sulfate. In some embodiments, the cation is a tertiary ammonium cation. In some embodiments, the tertiary ammonium cation is a trimethyl, tributyl, triethyl or tripropyl ammonium cation. In some embodiments, the glycoprotein or glycopeptide of interest is in a mixture of glycoproteins. In some embodiments, the glycoprotein or glycopeptide of interest is in a cell lysate, blood serum, blood plasma, is a fusion protein, or is a cell membrane protein. In some embodiments, the method further comprises the steps of heating a solution comprising the glycoprotein or glycopeptide and the ammonium cation sulfate detergent or the ammonium cation sulfonate detergent to a temperature ranging from about 80° to about 120° C., maintaining the mixture within the temperature range for time T, and then cooling said solution. In some embodiments, the temperature range is from about 90° to about 100° C. In some embodiments, the solution is cooled to a temperature of about 35-60° C. following time T. In some embodiments, the solution is cooled to a temperature of about 50° C. In some embodiments, time T is between about 1 to about 10 minutes. In some embodiments, time T is about 3 minutes. In some embodiments, the method further comprises releasing glycans from the denatured glycoprotein or glycopeptide by incubating the denatured glycoprotein or glycopeptide with a deglycosylation enzyme for a time sufficient to release said glycans, thereby forming a solution comprising the glycans, the glycoprotein or glycopeptide from which said glycans have been released, and the ammonium cation sulfate or sulfonate detergent. In some embodiments, either the glycoprotein or glycopeptide or the deglycosylation enzyme is immobilized on a solid support. In some embodiments, the denatured glycoprotein or glycopeptide is immobilized on a solid support prior to being contacted with the deglycosylation enzyme. In some embodiments, the deglycosylation enzyme is an amidase. In some embodiments, the amidase is PNG F. In some embodiments, the released glycans are labeled following release from the glycoprotein or glycopeptide. In some embodiments, the released glycans are released as β-glycosylamines. In some embodiments, the label is fluorescent. In some embodiments, the labeled released glycans are analyzed. In some embodiments, the analysis is selected from the group consisting of high-performance liquid chromatography, hydrophilic interaction chromatography, nuclear magnetic resonance, fluorescence analysis, Western blotting, gel electrophoresis, capillary electrophoresis, microfluidic separation, and mass spectrometry or a combination of any two or more of these. In some embodiments, the analyzing is by detecting a fluorescent signal from said labeled released glycans. In some embodiments, the denatured glycoprotein or glycoprotein (now deglycosylated) from which said glycans have been released is analyzed. In some embodiments, the analyzing of the glycoprotein or glycoprotein from which glycans have been released is by high-performance liquid chromatography, hydrophilic interaction chromatography, nuclear magnetic resonance, Western blotting, gel electrophoresis, fluorescence analysis, capillary electrophoresis, microfluidic separation, mass spectrometry, or a combination of two or more of any of these.

In some embodiments, the analysis is by mass spectrometry. In some embodiments, the solution further comprises a reductant, an alkylant, an additional organic solvent denaturant, a chaotrope, or a combination of any of these. In some embodiments, the ammonium cation sulfate detergent or ammonium cation sulfonate detergent is removed prior to the analyzing. In some embodiments, the removing of the ammonium cation sulfate detergent or the ammonium cation sulfonate detergent comprises flowing the solution comprising the released glycans, the glycoprotein or glycoprotein from which the glycans have been released, and the detergent into a solid phase extraction device to remove the detergent from the solution.

In a further group of embodiments, the invention provides methods of denaturing a glycoprotein or glycopeptide of interest in vitro, comprising incubating the glycoprotein or glycopeptide in vitro with a solution comprising effective amounts of (a) a compound of the formula: R—Y-.M+, in which: R is a saturated or unsaturated straight chain aliphatic group with 8-13 carbon atoms; Y- is a sulfate or sulfonate anion; M+ is a cation of an element in periodic table group 1; and, the dot indicates that the cation is ionically, not covalently, associated with the Y- anion, and either (b) an ammonium cation detergent comprising: (i) an aliphatic chain of 8-24 carbons, (ii) a carboxylate anion covalently attached to the aliphatic chain and, (iii) a tertiary or quaternary ammonium cation ionically, not covalently, associated with the carboxylate anion, or (b') a molar excess of quaternary ammonium cations, or of tertiary ammonium cations, or of both. In some embodiments, R is an aliphatic group having 12 carbons. In some embodiments, Y- is a sulfate anion. In some embodiments, the tertiary or quaternary ammonium cation of said ammonium cation detergent is a quaternary ammonium cation. In some embodiments, the ammonium cation detergent is tetramethylammonium acetate or tetramethylammonium laurate. In some embodiments, the molar excess of said quaternary ammonium cations or tertiary ammonium cations is of quaternary ammonium cations. In some embodiments, the quaternary ammonium cation is selected from the group consisting of:

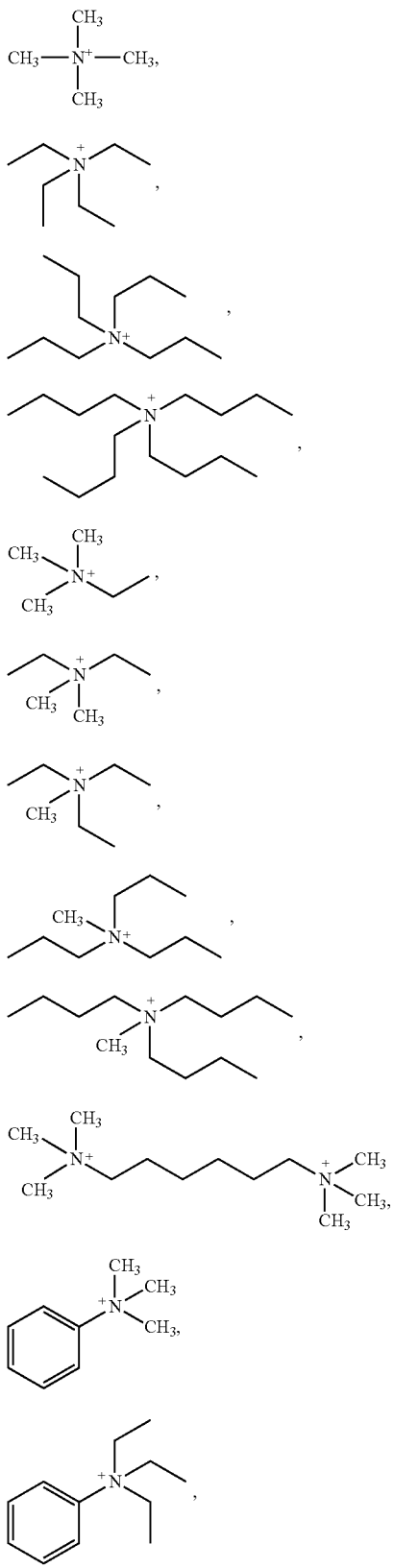

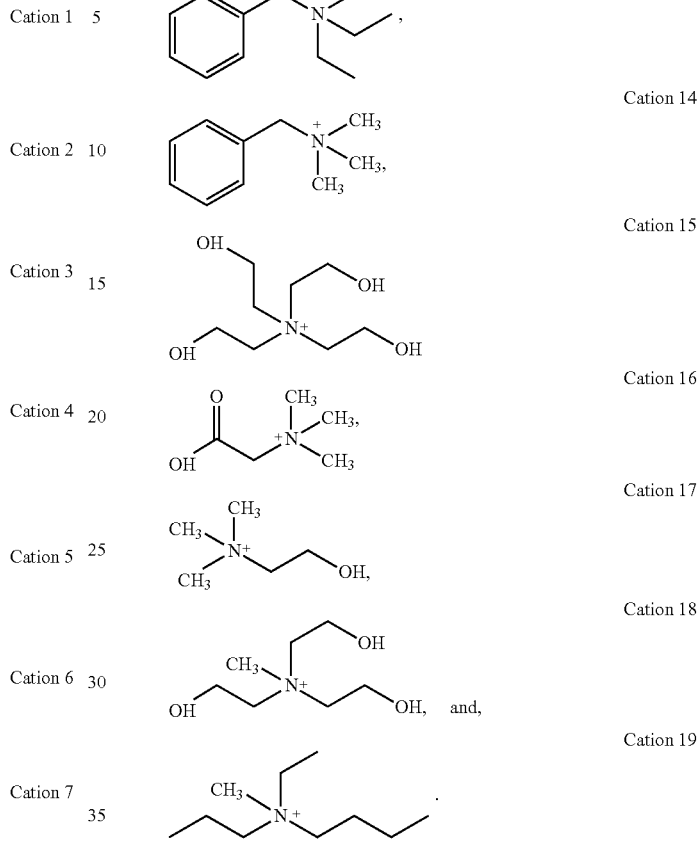

In some embodiments, the quaternary ammonium cation is tetramethyl ammonium. In some embodiments, the molar excess of quaternary ammonium cations is of tetramethyl ammonium cations.

BRIEF DESCRIPTION OF THE DRAWINGS

FIG. 1 is a table showing the comparative results of studies using sodium dodecyl sulfate and tetramethyl ammonium lauryl sulfate as detergents in a deglycosylation protocol on a series of glycoproteins and mixtures of glycoproteins. To permit ready comparison of how well each detergent served in the deglycosylation protocol, the amount of glycans released from each glycoprotein or mixture of glycoproteins in the assay in which tetramethyl ammonium dodecyl sulfate was used as the detergent was normalized to 100%, and the amount released then compared to the amount of glycan released when SDS was used as the detergent in the same deglycosylation protocol on the same glycoprotein. hIgG: mixture of human IgG antibodies. hIgA: mixture of human IgA antibodies. hIgM: mixture of human IgM antibodies. "Nist mAb": An antibody provided by the National Institute of Standards and Technology ("NIST"), as reference material 8671.

DETAILED DESCRIPTION

Figure 2:
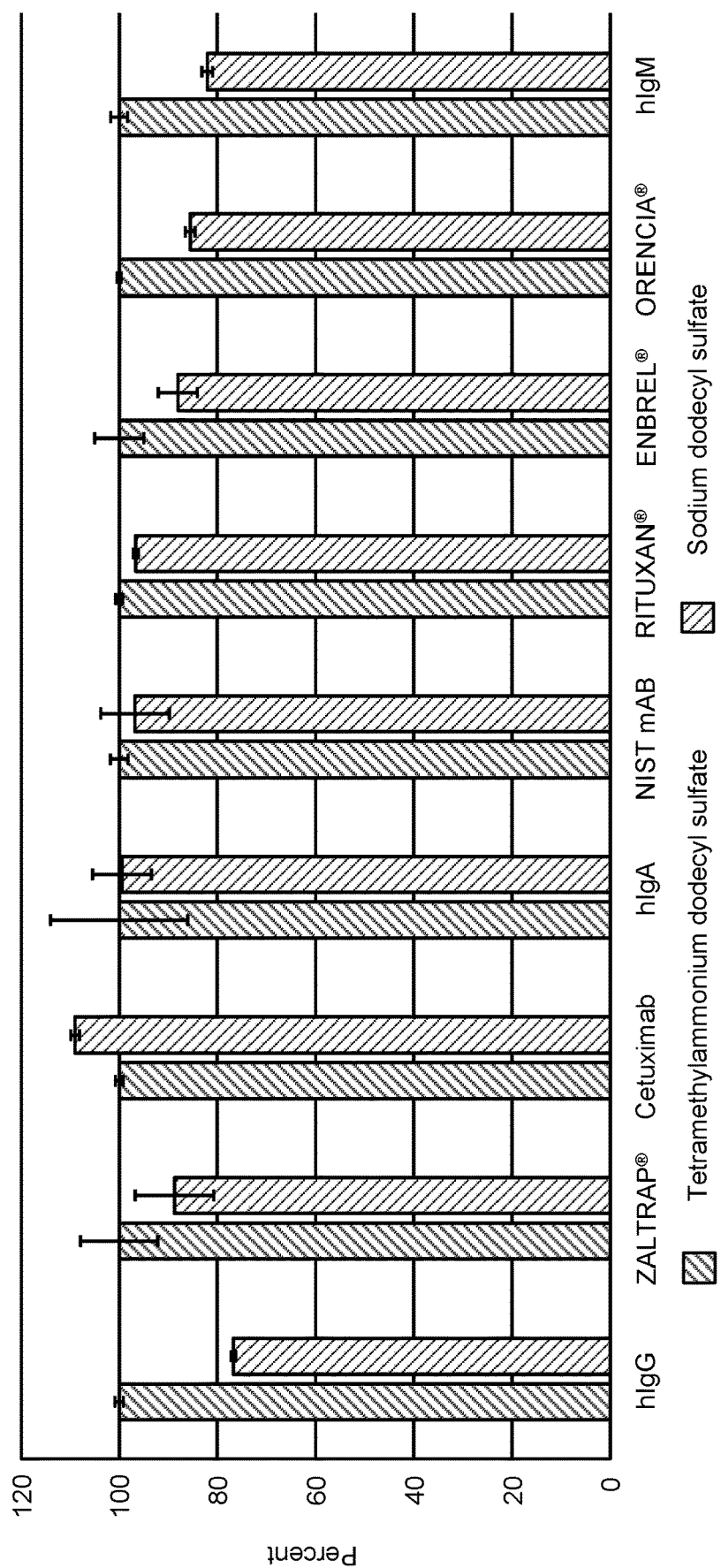
FIG. 2 presents the results of the comparative studies reported in FIG. 1 in the form of a graph. The error bars represent the results of three replicates. The "tetramethyl-ammonium dodecyl sulfate" referred to on FIG. 2 is the same compound referred to as "tetramethyl ammonium lauryl sulfate" in FIG. 1.

Which carbohydrates, or glycans, are attached to a glycoprotein is important to understanding the pharmacokinetics, immunogenicity, and potential therapeutic effectiveness of the glycoprotein. Accordingly, removing the glycans and analyzing them to determine which glycans are attached to a given glycoprotein has become an important aspect of quality control for glycoproteins, such as antibodies and other biologics, intended for therapeutic use. Further, analyzing the aglycosylated glycoprotein after its glycans have been removed has also become important for confirming the composition of the aglycosylated protein.

Unfortunately, some glycoproteins, especially some antibody and antibody-derived therapeutics, are resistant to enzymatic deglycosylation by standard protocols, especially those involving release of N-glycans by the exemplar enzyme PNGase F. Since there is no way to determine in advance whether any particular glycoprotein of interest is easy or hard to deglycosylate by enzymatic release of the glycans, it is generally determined empirically by subjecting the glycoprotein to an enzymatic deglycosylation protocol intended to remove N-glycans, O-glycans, or both, known to be present on the glycoprotein and analyzing the molecular weight of the protein following the procedure to determine whether the molecular weight indicates that the N-glycans, O-glycans, or both, present on the glycoprotein have been removed or that some remain attached. Glycoproteins are typically denatured prior to enzymatic deglycosylation so that the enzyme has access to glycosylation sites which otherwise might be hidden or blocked by the protein's secondary or tertiary structure. Often, a detergent is used to solubilize the glycoprotein as part of the denaturation step. The detergent may also participate in denaturation of the glycoprotein, and may be referred to as a denaturant in addition to being referred to as a detergent. It would be convenient to have additional detergents that can work across a range of glycoproteins from those relatively easy-to-deglycosylate to those relatively hard-to-deglycosylate in an attempt to reduce the number of glycoproteins for which protocols have to be adopted.

Experiments were performed in attempts to find detergents that would be effective in enzymatic deglycosylation protocols over a range of glycoproteins. As antibodies and antibody-derived glycoproteins are increasingly important as therapeutic agents, some of our studies focused on examining the deglycosylation of a selection of some of the currently-available antibody and anti-derived agents.

In initial studies underlying the present invention, we found that fatty acid salts with alkali metal cations, such as sodium laurate, were good detergents for deglycosylation of many glycoproteins. We further found that substituting an exemplar quaternary ammonium cation, tetramethyl ammonium, in place of the alkali metal, sodium, in sodium laurate, resulted in deglycosylation about as good as that when using sodium laurate for many glycoproteins, but in markedly better deglycosylation of some glycoproteins. It was found, for example, that in the presence of the exemplar quaternary ammonium cation fatty acid salt, a deglycosylation protocol resulted in the release of 21% more glycan from IgM than did the same protocol using the fatty acid salt, but with an alkali metal cation rather than the quaternary ammonium cation. Thus, we found that quaternary ammonium fatty acid salts are superior to fatty acid salt detergents for denaturing glycoproteins for enzymatic deglycosylation protocols; and particularly for deglycosylation protocols for antibodies and antibody-derived glycoproteins. References herein to "quaternary ammonium carboxyl salts" or "quaternary ammonium fatty acid salts" or "quaternary ammonium fatty acid detergents" refer to compounds with a quaternary ammonium cation, and an aliphatic chain attached to a carboxylate anion.

Surprisingly, when we tested an exemplar quaternary ammonium cation-sulfate detergent, tetramethylammonium dodecyl sulfate, with a sulfate anion replacing the laurate of the corresponding quaternary ammonium cation fatty acid detergent, we got markedly better results than were obtained with the exemplar quaternary ammonium fatty acid salt in deglycosylating glycoproteins.

The detergents were tested on a recombinant fusion protein Ziv-aflibercept, a cancer therapeutic sold under the name ZALTRAP®. To permit ready comparison, the glycans released by the exemplar quaternary ammonium-sulfate detergent, tetramethylammonium dodecyl sulfate, were treated as representing 100% release of glycans from Ziv-aflibercept, and that amount was compared to the amount of glycans released from Ziv-aflibercept using the same protocol and the corresponding exemplar quaternary ammonium fatty acid salt detergent, tetramethylammonium dodecyl laurate. Use of the quaternary ammonium fatty acid salt detergent resulted in the release of 80-90% of the amount of glycans released from ZALTRAP® by the quaternary ammonium-sulfate detergent. Tests with other hard-to-deglycosylate glycoproteins confirmed that the exemplar quaternary ammonium-fatty acid detergent tested was not as successful at deglycosylating such glycoproteins as the exemplar quaternary ammonium-sulfate detergent. Accordingly, we concluded that quaternary ammonium-sulfate detergents are surprisingly better detergents for denaturing glycoproteins for enzymatic deglycosylation protocols than are either quaternary ammonium-fatty acid detergents or fatty acid detergents.

Sodium dodecyl sulfate ("SDS," also known as sodium lauryl sulfate) is a detergent widely used to denature and solubilize proteins, particularly before subjecting them to electrophoresis, and is commonly used to denature glycoproteins in deglycosylation protocols. As a denaturant for deglycosylation applications, SDS is often used in combination with a non-ionic surfactant, typically NP-40, after the denaturing step but prior to adding the enzyme to prevent denaturation of the enzyme. A series of studies was conducted to determine how the exemplar quaternary ammonium-sulfate detergent, tetramethyl ammonium dodecyl sulfate, compared to SDS.

In the studies reported herein, nine exemplar glycoproteins or mixtures of glycoproteins were subjected to enzymatic deglycosylation following denaturing using either an exemplar quaternary ammonium-sulfate detergent, or SDS. To allow ready comparison, the amount of glycans released from each glycoprotein or mixture by digestion following denaturing with tetramethyl ammonium lauryl sulfate was considered to be a 100% release, and that amount was then compared to the amount released from the same glycoprotein or glycoprotein mixture following denaturion with SDS. Surprisingly, for four out of nine of the glycoproteins or glycoprotein mixtures, denaturing with SDS resulted in the release of significantly fewer glycans than did the use of the exemplar quarternary ammonium sulfate detergent, and for a mixture of human IgGs, denaturing with SDS resulted in the release of almost 25% less glycan than did denaturing with the quarternary ammonium sulfate detergent. For a mixture of hIgM antibodies, denaturing with SDS resulted in the release of 18% less glycan than did denaturing with the quarternary ammonium sulfate detergent. For the therapeutic biologic drug ORENCIA®, denaturing with SDS resulted in the release of almost 15% less glycan than did denaturing with the quarternary ammonium sulfate detergent. For three of the nine glycoproteins or mixtures, using SDS to denature the glycoprotein resulted in about the same release of glycan compared with the amount released following denaturation of the same glycoprotein with the quarternary ammonium sulfate detergent. Only in the case of one glycoprotein did denaturing with SDS result in the release of more glycan than did the use of quarternary ammonium sulfate detergent, and in that case the difference was less than 10%. The results show that the exemplar quarternary ammonium sulfate detergent provided generally better or equal results to using SDS in the deglycosylation protocol, and in many cases, provided surprisingly better results compared SDS, both for some hard-to-denature glycoproteins and for mixtures of glycoproteins.

As noted above, enzymatic deglycosylation protocols in which SDS is used as a detergent typically recite the addition of a non-ionic detergent prior to introducing the enzyme to avoid denaturing it. Studies with an exemplar quaternary ammonium-sulfate detergent revealed that no non-ionic detergent was needed. Indeed, the studies showed that the presence of a non-ionic detergent is preferably not used. Thus, embodiments of the inventive methods allow eliminating a reagent used in typical protocols.

Given the results with an exemplar quarternary ammonium sulfate detergent, it is believed that other detergents which provide a quaternary ammonium cation, an aliphatic chain, and a sulfate anion will also be surprisingly useful detergents for denaturing glycoproteins compared to detergents with an aliphatic chain and a sulfate anion, but a counterion different from a quaternary ammonium cation or a tertiary ammonium cation, as further discussed below. It is further believed that, given the structural and functional similarity of a sulfonate anion to a sulfate anion, that detergents with a quaternary ammonium cation, and an aliphatic chain covalently attached to a sulfonate anion will also be surprisingly useful detergents for the same purposes. Given the difference in charge between the sulfate and the sulfonate anions, we believe that, between detergents differing only between a sulfate versus a sulfonate anion, the one with the sulfate anion will be the better detergent. Further, given the structural and functional similarity of a tertiary ammonium cation to a quaternary ammonium cation, we expect tertiary ammonium cations to form effective detergents with sulfate or sulfonate anions. In some embodiments, the detergents have a quaternary ammonium cation, an aliphatic chain, and a sulfate anion. In some embodiments, the detergents have a quaternary ammonium cation, an aliphatic chain, and a sulfonate anion. In some embodiments, the detergents have a tertiary ammonium cation, an aliphatic chain, and a sulfate anion. In some embodiments, the detergents have a tertiary ammonium cation, an aliphatic chain, and a sulfonate anion.

As noted in the Background, once the glycoproteins or glycopeptides are denatured, they are frequently subjected to enzymatic digestion to release N-linked carbohydrates as glycosylamines, which are then typically labeled with an amine-reactive dye. Primary and secondary ammonium salts are less preferred for use in the inventive methods because they could compete with glycans released as glycosylamines following enzymatic digestion and reduce the availability of the glycosylamines for labeling. Tertiary and quaternary ammonium sulfate and sulfonate detergents are expected to be useful for denaturing the glycoprotein but not to react with glycosylamines released from the glycoproteins or glycopeptides of interest by enzymatic digestion. To avoid constant repetition of "glycoprotein or glycopeptide," references to deglycosylation or analysis of a "glycoprotein" herein encompass deglycosylation or analysis of a "glycopeptide" unless otherwise required by context.

Ammonium Cation Sulfate and Sulfonate Detergents

As reported above, an exemplar quaternary ammonium sulfate detergent, was surprisingly more effective in denaturing glycoproteins than a like quaternary ammonium detergent based on a fatty acid, and then the commonly used detergent SIDS. These results indicate that effective detergents can be made following the formula of the following formula:

$$R—Y^-.C^+, \text{ in which:} \qquad \text{Formula 1}$$

R is a saturated or unsaturated aliphatic group with 8-22 carbon atoms;

$Y^-$ is sulfate or sulfonate;

$C^+$ is a quaternary ammonium cation or a tertiary ammonium cation; and, the dot indicates that the cation is ionically, not covalently associated, with the $Y^-$.

In preferred embodiments, the aliphatic group is saturated. In some embodiments, $Y^-$ is sulfate. In some embodiments. $Y^-$ is sulfonate. In some embodiments in which $Y^-$ is a sulfate or sulfonate, the aliphatic group is 8-20, 9-19, 9-18, 9-17, 9-16, 10-16, 10-15, 10-15, 11-14, 11-13, or 12 carbon atoms in length, with each succeeding range or number stated being more preferred than the one preceding it. An aliphatic group of twelve carbons is particularly preferred. The aliphatic group is preferably straight. In some embodiments, it can be in a ring configuration. The aliphatic group is covalently attached to the $Y^-$. As used herein, the phrase "ammonium sulfate detergent" or "ammonium sulfonate detergent" refers to a detergent of Formula 1. As used herein, the phrases "quaternary ammonium sulfate detergent" and "quaternary ammonium sulfonate detergent" refer to a detergent of Formula 1 in which $C^+$ is a quaternary ammonium cation. As used herein, the phrases "tertiary ammonium sulfate detergent" and "tertiary ammonium sulfonate detergent" refer to a detergent of Formula 1 in which $C^+$ is a tertiary ammonium cation.

Quaternary ammonium cations have the advantage of maintaining their positive charge independent of the pH of their environment, whereas the charge of primary, secondary and tertiary ammonium cations can vary according to the surrounding pH. It is anticipated that most deglycosylation procedures and other denaturing procedures will be conducted at pHs at which tertiary ammonium cations will maintain their positive charge and can be useful as cations of compounds of Formula 1, For example, the ammonium cation can be a tertiary ammonium cation, such as trimethyl ammonium, triethyl ammonium, tripropyl ammonium or tributyl ammonium. Primary and secondary ammonium cations are expected to be less useful as cations for detergents, as the nitrogen may be accessible to react with amine-reactive dyes or other reagents.

In some embodiments, the cation is a quaternary ammonium cation. As used herein, "quaternary ammonium cation" refers to a moiety having the formula $N+^1R_1R_2R_3R_4$, wherein each R can be the same or different and are chosen from aryl or alkyl, can be saturated or unsaturated, can be unsubstituted or substituted, may contain atoms other than carbon or hydrogen in the chain or ring or attached to the chain or ring, including carbon-bonding substituents such as sulfur, oxygen, nitrogen, boron, or a halogen, and functional groups containing any of these, and can be another quaternary group. In some preferred embodiments, the quaternary ammonium cation is selected from the group consisting of:

Cation 1

CH₃—N⁺(CH₃)(CH₃)—CH₃

Cation 2

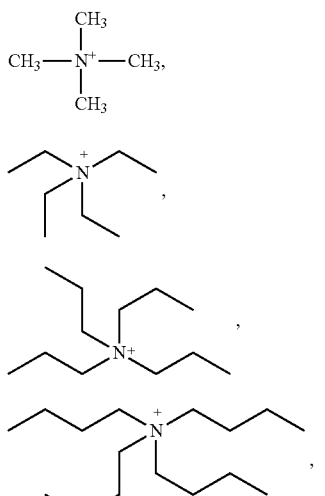

Cation 3

Cation 4

Cation 5

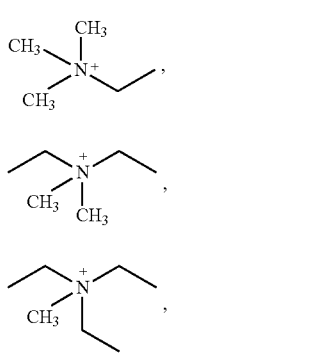

Cation 6

Cation 7

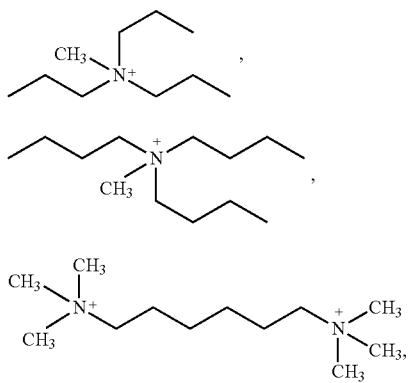

Cation 8

Cation 9

Cation 10

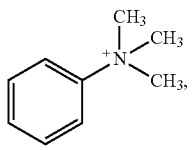

Cation 11

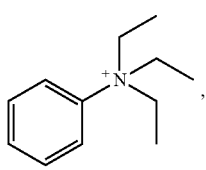

Cation 12

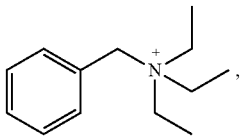

Cation 13

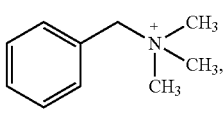

Cation 14

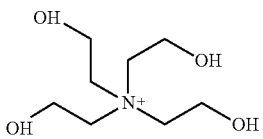

Cation 15

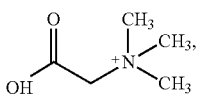

Cation 16

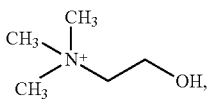

Cation 17

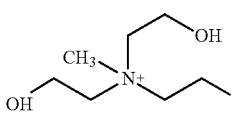

Cation 18

, and,

Cation 19

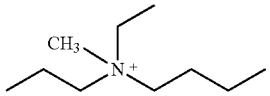

Cations with a smaller number of atoms are generally preferred over cations with a larger number of atoms.

In some embodiments, the cation can instead be a tertiary ammonium cation. As used herein, a "tertiary ammonium cation" refers to a moiety having the formula $HN^{+1}R_1R_2R_3$, wherein $R_1$, $R_2$, and $R_3$, can be the same or different and are chosen from aryl or alkyl, can be saturated or unsaturated, can be unsubstituted or substituted, may contain atoms other than carbon or hydrogen in the chain or ring or attached to the chain or ring, including carbon-bonding substituents such as sulfur, oxygen, nitrogen, boron, or a halogen, and functional groups containing these, and can be another tertiary group.

Fatty acid salts of ammonium cations which are not commercially available can be synthesized by reacting the fatty acid of choice with the hydroxide conjugate base. For example, tetramethylammonium laurate can be synthesized by reacting lauric acid with tetramethyl ammonium hydroxide and we made tetraethyl ammonium laurate, tetrapropyl ammonium laurate, and tetrabutyl ammonium laurate by the same process. The hydroxide conjugate bases of some, if not all, of the quaternary ammonium cations listed are commercially available. Any that are not can be synthesized by methods well known in the art, such as reacting a salt of the quaternary ammonium cation with a strong base. For example, tetramethyl ammonium hydroxide is typically made by mixing tetramethylammonium chloride and potassium hydroxide in dry methanol.

Ammonium cation sulfate and sulfonate detergents can be made by any convenient method known in the art, such as by acid based neutralization, as discussed above, or by ion exchange. A procedure for preparing an exemplar quaternary ammonium sulfate cation detergent by ion exchange is set forth in the Examples.

Combinations of Ammonium Salts and Periodic Table Group 1 Detergents

It is believed that sulfate or sulfonate detergents having a cation of an element of periodic table group 1 can be used in combination with quaternary ammonium cations and tertiary ammonium cations to form unexpectedly powerful detergents for denaturing glycoproteins for deglycosylation. The quaternary ammonium cations or tertiary ammonium cations can be contributed by, for example, a quaternary ammonium fatty acid salt.

These detergents comprising elements in periodic table group 1 have the following formula:

Formula 2: R—Y−.M+, in which:

R is a saturated or unsaturated straight chain aliphatic group with 8-13 carbon atoms;
Y− is a sulfate or sulfonate anion;
M+ is a cation of an element of periodic table group 1; and, the dot indicates that the cation is ionically, rather than covalently, associated with the Y− anion.

It is believed compounds of this formula will be good detergents to be mixed with one or more quaternary or tertiary ammonium cation salts, or quaternary or tertiary ammonium cation cations, for denaturing glycoproteins or glycopeptides in deglycosylation protocols. In preferred embodiments, the aliphatic group is saturated. In preferred embodiments, the aliphatic group is 10-12 carbons in length. In some embodiments, Y− is a sulfate anion. In some embodiments, Y− is a sulfonate anion. For convenience of reference, compounds of Formula 2 may also sometimes be referred to herein as "M+ detergents."

Given the structural similarity of tertiary ammonium salts to quaternary ammonium salts, it is also expected that tertiary ammonium salts can be used with a M+ detergent of Formula 2 to achieve similar results. An excess of quaternary or tertiary ammonium cations can be provided by any convenient means known in the art. Primary and secondary ammonium salts are less preferred because they could compete with glycans released as glycosylamines during a subsequent enzymatic digestion and thus would require an additional cleanup step in a deglycosylation protocol to remove them after the denaturing step but before the enzymatic digestion step.

In some embodiments, the solution contains quaternary ammonium cations. In some embodiments, the solution comprises a molar excess of quaternary ammonium cations compared to the compound of Formula 2. In some embodiments, the solution contains tertiary ammonium cations. In some embodiments, the solution contains a molar excess of tertiary ammonium cations to the compound of Formula 2.

Use of the mixtures and detergents described above allows methods of releasing glycans from glycoproteins that reduce the time needed for workflows to release glycans from glycoproteins and then to analyze the released glycans, the protein from which the glycans have been released, or both.

Mixtures of M+ Detergents and Ammonium Cation Salts for Use in Preparing Glycoproteins for Deglycosylation Protocols It is believed a mixture of a compound of Formula 2 and a quaternary ammonium salt in a deglycosylation protocol allows rapid and effective enzymatic deglycosylation of a range of antibody and antibody-derived glycoproteins. The effective deglycosylation is expected to be due at least in part to the detergent effect of the mixture in allowing access of PNGase F to sites at which N-glycans are attached to the protein. It is further believed that this is due in part to the interaction of the quaternary ammonium cation with the sulfated aliphatic chain contributed by the compound of Formula 2 to the reaction mixture at the pH of the solution.

Salts of other quaternary ammonium cations can contribute quaternary ammonium cations to the mixture and result in effective deglycosylation of a range of glycoproteins. Such salts are suitable so long as they are capable of dissociating under the pH and temperature conditions to be utilized in the deglycosylation procedure. Whether any particular salt can be used in the inventive methods can be readily determined by simply running a deglycosylation protocol in parallel on two aliquots of the same glycoprotein, preferably an antibody or an antibody-derived glycoprotein, with the protocol differing only in the detergent mix used, and comparing the amounts and types of glycans released from each aliquot. Test salts that are suitable for use in the inventive methods will result in the release of at least all of the same glycans as are released by the reference salt, in amounts equal to, greater than, or not more than 5% less than the amounts released by the reference mix.

Due to their structural and functional similarity to quaternary ammonium cations, it is believed that salts of tertiary ammonium cations can also contribute ammonium cations to the mixture and result in effective deglycosylation of a range of glycoproteins. Secondary and primary ammonium cations are believed likely to work for effective deglycosylation, but are less preferred because they could interfere with later labeling of released glycans unless additional cleanup steps are introduced into the protocol.

Mixtures of Detergents of Formula 1 and of Formula 2

It is believed that combining a detergent of Formula 2 with an ammonium cation sulfate or sulfonate detergent of Formula 1 will be useful in unfolding glycoproteins while keeping them in solution, rendering sites on the glycoprotein accessible to the deglycosylation enzyme that might not be made accessible by either detergent used on its own. Accordingly, in some embodiments, mixtures of detergents of Formula 1 and of Formula 2 are used in the enzymatic deglycosylation of glycoproteins, and particularly of antibodies and antibody-derivatives.

Ammonium Fatty Acid Salts

As noted above, initial studies using a fatty acid salt bearing an exemplar quaternary ammonium cation, proved to be good detergent for denaturing and deglycosylating glycoproteins. The exemplar ammonium fatty acid salt tested, tetramethyl ammonium laurate, caused the release of as much glycan as did an exemplar fatty acid salt, sodium laurate, when used in deglycosylation protocols on a number of glycoproteins, but resulted in releasing significantly more glycan from some hard-to-deglycosylate proteins. A comparison was made of the relative ability of tetramethyl ammonium laurate and an exemplar alkali metal fatty acid salt, sodium laurate, to serve as a detergent in denaturing glycans in an exemplar deglycosylation protocol. The detergents were tested on 18 different glycoproteins, including a number of FDA-approved therapeutic antibodies, and the resulting released glycans were analyzed. Previous work with similar data sets indicated that greater than a 5% difference in glycan release is significant.

The quaternary ammonium salt tetramethyl ammonium laurate and the alkali metal salt sodium laurate were also tested as detergents on complex mixtures of glycoproteins. First, the detergents were tested on cell lysates of Chinese hamster ovary ("CHO") cells. Cell lysates contain, among other glycoproteins, membrane proteins. As noted by \Naas et al., Anal. Chem., 2014, 86(3):1551-1559, membrane proteins are hard to subject to enzymatic digestion due to their hydrophobic properties. Second, the detergents were tested on mammalian blood serum. In both cases, the exemplar alkali metal fatty acid salt and glycoprotein mixture precipitated after the denaturation, interfering with the release of glycans, while the quaternary ammonium fatty acid salt and glycoprotein mixture remained in solution and allowed enzymatic release of glycans present in the sample.

Based on the results with two fusion proteins and two complex glycoprotein mixtures, ammonium cation fatty acid detergents were better in deglycosylation protocols for fusion proteins, particularly those containing Fc portions of antibodies, and for complex glycoprotein mixtures (including those containing membrane proteins) than are alkali metal or alkali earth metal fatty acid detergents, while working as well as alkali metal or alkali earth metal fatty acid detergents in deglycosylation protocols for glycoproteins such as antibodies.

The glycosylamines were released by enzymatic digestion and were then labeled with an amine-reactive dye. Embodiments in which the denaturant is present during the deglycosylation step is advantageous because it helps prevent the glycoprotein from refolding and perhaps rendering some sites once again inaccessible to the enzyme before deglycosylation can occur.

Ammonium Cation Detergents

As noted, our initial studies involved detergents having a quaternary ammonium cation and a fatty acid chain terminating in a carboxylate (an "ammonium carboxylate detergent"). We then discovered that an exemplar detergent with a quaternary ammonium cation and a sulfate anion was surprisingly better than the like detergent with a carboxylate anion. Accordingly, in some embodiments, the inventive compositions, methods, and kits employ a tertiary or quaternary ammonium cation and a sulfate or sulfonate anion. In other embodiments, the inventive compositions, methods, and kits employ a compound of Formula 2 and a tertiary or quaternary ammonium cation detergent, such as a quaternary ammonium sulfate detergent or a quaternary ammonium carboxylate detergent.

The initial studies conducted with an exemplar quaternary ammonium carboxylate detergent showed it was useful in denaturing complex mixtures of glycoproteins and other proteins found in cell lysates and mammalian blood serum. Given the surprisingly better results in deglycosylating glycoproteins and mixtures of glycoproteins that we obtained using an exemplar quaternary ammonium sulfate detergent compared to the exemplar quaternary ammonium carboxylate detergent, it is believed that tertiary ammonium sulfate detergents and quaternary ammonium sulfate detergents, and tertiary ammonium sulfonate and quaternary ammonium sulfonate detergents, will likewise prove surprisingly more useful in denaturing complex mixtures of glycoproteins and other proteins found in cell lysates and mammalian blood serum than are tertiary or quaternary ammonium carboxylate detergents.

It is expected that tertiary ammonium sulfate and sulfonate detergents and quaternary ammonium sulfate and sulfonate detergents, and particularly tertiary or quaternary ammonium sulfate detergents, will remain soluble with a somewhat longer aliphatic chain than fatty acid-based detergents, and thus in some embodiments may be 8-22 carbons long. In some embodiments, the aliphatic chain may be 8-21 carbons long, in some embodiments may be 8-20 carbons long, in some embodiments may be 8-19 carbons long, in some embodiments may be 8-18 carbons long, in some embodiments may be 8-17 carbons long and in some embodiments may be 8-16 carbons long, while in still others, the chain may be 8-15 carbons long, in some embodiments may be 8-14 carbons long, and in some other embodiments may be 8-13 carbons long. In some preferred embodiments, the aliphatic chain is saturated. In some embodiments, the aliphatic chain is unsaturated.

Lauric acid, which has 12 carbons, is one preferred for making ammonium cation sulfate and sulfonate detergents, with fatty acids with 11 carbons being next preferred. In some embodiments, the fatty acid used to form the salt has 12 carbons and is saturated. In some embodiments, the fatty acid used to form the salt has 11 carbons and is saturated. It is noted that "lauric acid" and the other trivial names for fatty acids refer to acids bearing the carboxylic acid end. Ammonium cation sulfate and sulfonate detergents derived from such fatty acids are often referred to by the cation, the length of the aliphatic chain, and the anion, such as "triethanol dodecanoic sulfate," "trimethanol decanoic sulfonate", or tributyl tetradecanoic sulfate." This practice is not universally followed as, for example, "ammonium lauryl sulfate" is an anionic surfactant commonly found as an ingredient of shampoos and body washes, while the IUPAC name can state the chain length first, then the ammonium cation, then the anion, as in "octadecyl trimethyl ammonium sulfate" or "hexadecyl-trimethylammonium sulfonate." The particular nomenclature chosen is not important.

Branched fatty acid chains do not seem to be useful. In some embodiments, however, the fatty acid can have 8-13 carbons and be in a ring configuration.

Use of Formula 1 and Formula 2 Detergents as Reagents to Denature Other Proteins As reported in the Examples, an exemplar quaternary ammonium sulfate detergent proved surprisingly useful in denaturing glycoproteins and glycoprotein mixtures as part of a deglycosylation protocol. These results indicate that tertiary and quaternary ammonium sulfate and sulfonate detergents, will also be useful reagents for other proteolytic, analytic, and diagnostic protocols, such as in denaturing proteins prior to conducting a Western blot, and in denaturing a fusion protein or glycoproteins or proteins in a complex mixture, such as a cell lysate or blood serum or plasma. Tertiary and quaternary ammonium sulfate and sulfonate detergents are expected to be particularly useful for denaturing cell membrane proteins.

Concentrations

Typically, mixtures in which a compound of Formula 2 is mixed with a quaternary or tertiary ammonium cation salt, such as an ammonium cation fatty acid salt, will be 0.50% to 3.0%, 0.75-2.50%, 0.75-2.25%, 1.0-2.0%, or 1.0-1.50% Formula 2 detergent, with each successive range being more preferred to the one before it. Good results can be obtained using a concentration of 1.25%, which concentration is the most preferred. The quaternary or tertiary ammonium cation salt is preferably present at 10 mM-150 mM, 10-125 mM, 20-100 mM, 25-100 mM, 30-100 mM, 30-90 mM, 30-80 mM, 30-75 mM, 40-70 mM, 40-65 mM, 40-60 mM, or 45-55 mM. Good results were obtained using 50 mM of exemplar quaternary ammonium detergents. The mixtures were in an aqueous base. The pH can be between 6 and 9.5 and may be a pH of 7-9, or of 8-9. Some of the underlying studies were performed in solutions without significant buffering capacity, at a pH of 8.5, which is a preferred pH for some embodiments.

In embodiments in which a quaternary or tertiary ammonium sulfate or sulfonate (Formula 1) detergent is used, the detergent will typically be used in a concentration of 0.01 to 2.5%, more preferably 0.05 to about 2.0%, still more preferably 0.1 to about 1.5%, and in still more preferred embodiments, 0.01 to about 1%, where the term "about" means plus or minus 0.05% and the concentration is measured as volume/volume. Persons of skill are aware that glycoproteins differ in how hard they are to denature and that how hard any particular glycoprotein is to denature is usually determined empirically. If a particular glycoprotein proves to be hard to denature, the concentration of the detergent can be at the higher end of the stated amounts. As glycoproteins that are hard to denature are typically denatured at a higher temperature, a hard-to-denature glycoprotein will usually also be subjected to a higher temperature.

Use of Multiple Detergents to Provide More Complete Solubilization

Glycoproteins are usually denatured in a buffer which already contains one or more salts. For example, phosphate buffered saline is a common buffer which, as its name states, is a saline solution. Some combinations of ammonium cation sulfate or sulfonate detergent in combination with the salt already in the buffer, or of a mixture of a Formula 2 detergent and a quaternary or tertiary ammonium cation sulfate or sulfonate salt, in combination with salt already in the buffer, may result in a concentration of salt as to cause the glycoprotein to precipitate. Where the practitioner intends to perform an assay using a new combination of a particular ammonium cation detergent and a particular buffer with a particular glycoprotein, or of a mixture of a Formula 2 detergent and an quaternary or tertiary ammonium cation sulfate or sulfonate detergent, it is good practice to combine a small amount of these components to verify that the glycoprotein remains in solution. If the glycoprotein precipitates, which is easily observed visually, that indicates that the particular combination is too salty for use with that glycoprotein and that the practitioner should select a buffer with a lower salt concentration or a different ammonium cation detergent. As persons of skill are aware, these kinds of preliminary tests to find combinations of reagents suitable for use with a particular glycoprotein are usual in this art.

Persons of skill will further appreciate that the ease of denaturing glycoproteins depends on a range of factors, including their secondary and tertiary structure, and some glycoproteins are resistant to denaturing even under conditions that would denature most other glycoproteins. In some embodiments, particularly with regard to denaturing a glycoprotein known to be hard to denature or one proving in practice to be hard to denature completely using an ammonium cation sulfate or sulfonate detergent, the practitioner may wish to also add one or more additional detergents or additional organic solvent denaturants, such as acetonitrile or tetrahydrofuran, or a chaotrope, such as urea or guanidinium chloride.

As noted in the Background, current protocols often combine the anionic detergent SDS with a non-ionic detergent. We have found that a nonionic detergent is not needed with the exemplar quaternary ammonium detergents. Accordingly, in preferred embodiments, a non-ionic detergent is not present during deglycosylation of target glycoproteins or glycopeptides.

A detergent of Formula 2 may be mixed with more than one ammonium cation salt at a time in an effort to improve solubilization of a glycoprotein or glycoprotein mixture for deglycosylation. Similarly, more than one Formula 2 detergent may be used with an ammonium cation salt or two such salts. In some embodiments, two or three different ammonium cation detergents may be combined in solution with the glycoprotein or mixture of glycoproteins to be denatured. In some of these embodiments, the ammonium cation of the two or the three salts is the same, but the anion is different. In other embodiments, the anion of two detergents is the same, but one of the detergents has a tertiary ammonium cation and the other a quaternary ammonium cation, or one has one tertiary cation and the other a different tertiary cation, or one has a first quaternary cation and the second has a second quaternary ammonium cation. In practice, there are diminishing returns as the number of detergents increases and while it might not be unusual to use two or three, it is unusual to see protocols calling for five or more.

The use of multiple detergents and salts can complicate cleanup and removal for downstream analytic steps. In some embodiments, the ammonium cation detergents are all quaternary ammonium sulfate detergents. In some embodiments, the ammonium cation detergents are all quaternary sulfonate detergents. In some embodiments, the detergents are of the same or of different types, but can be conveniently be removed by use of a suitable cleanup column. Persons of skill are knowledgeable about the use of these reagents and their removal after they have served their purpose.

Other Agents that May be Used During Denaturation of the Glycoprotein

The solution containing the glycoprotein and the ammonium cation detergent can contain further agents commonly used in protocols for deglycosylating glycoproteins. In particular, the solution can contain reductants, such as tris(2-carboxyethyl)phosphine, dithiothreitol (DTT), beta-mercaptoethanol (BME), alkylants, such as iodoacetamide, or a combination of reductants and alkylants. The solution can contain an organic solvent denaturant, such as acetonitrile, tetrahydrofuran, trifluoroethanol, or hexafluoroisopropanol and may contain a chaotrope, such as urea or guanidinium chloride. It is expected that persons of skill in denaturing and deglycosylating glycoproteins are familiar with the use of each of these types of reagents and the compounds usually used for these purposes.

Heating the Glycoprotein-Detergent Mixture to Speed Denaturation

To denature the glycoprotein, a solution containing the ammonium cation detergent of choice is added to the glycoprotein and the resulting mixture is incubated. In some embodiments in which the practitioner want to complete the denaturation more quickly, the mixture can be heated. In some embodiments, the mixture is heated to a high temperature (typically, 90° C., although for glycoproteins known to be hard to denature, it may be higher). In some embodiments, the mixture is heated as high as 100° C. In most embodiments, the mixture will not be heated higher than 100° C., although in some embodiments, the mixture may be heated as high as 120° C. Typically, the solution will be heated for a time between 1 minute and about 10 minutes, more preferably 2-7 minutes, still more preferably about 2-5 minutes, even more preferably about 3 to about 5 minutes and most preferably about 3 minutes. It is not expected that heating the mixture for more than about 5 minutes will improve the denaturation of the glycoprotein. As used herein in connection with a statement of a time, the term "about" means plus or minus 30 seconds.

Cooling

The denatured glycoprotein or glycopeptide will preferably be cooled before being deglycosylated by a deglycosylation enzyme, such as the exemplar deglycosylation enzyme PNGase F, both to avoid denaturing the deglycosylation enzyme once it is added and to permit the deglycosylation to occur at a temperature in a range at which the enzyme is most active. The solution containing the glycoprotein is preferably cooled to about 22-60° C., and more preferably about 35-55° C. In some preferred embodiments, the glycoprotein or glycopeptide is cooled to about 45-50° C. and most preferably about 50° C. Persons of skill will appreciate that for some equipment, the heat transfer from the apparatus to the reactants is not complete and that a temperature setting of the heating apparatus will result in the reactants being at a temperature several degrees cooler than the temperature setting, and will adjust accordingly. As used herein in connection with a temperature, the term "about" means plus or minus 1 degree C.

Deglycosylation

In some embodiments, the glycoprotein is deglycosylated by a deglycosylation enzyme. In some embodiments, the deglycosylation enzyme is an amidase. In some embodiments, the deglycosylation enzyme is the amidase PNGase F. In some embodiments, the deglycosylation enzyme is an endoglycosidase such as Endoglycosidase F1, Endoglycosidase F2, Endoglycosidase F3, or Endoglycosidase H. In some embodiments, the practitioner wishes to distinguish between any N-glycans that may be present on the glycoprotein from any O-glycans that may be present. In some embodiments, the enzymes mentioned above are used in connection with an ammonium cation detergent denaturation to provide a fast method of removing the N-glycans from the glycoprotein so that any O-glycans or glycosaminoglycans (GAGS) that may be on the glycoprotein can be analyzed. For example, the first digestion may be made using an enzyme to remove N-glycans, followed by a second enzymatic digestion with endo-alpha-N-acetyl-galactosaminidase to remove O-glycans. It is expected that persons of skill are familiar with the various enzymes used for enzymatic release of carbohydrates from glycoconjugates in general and from glycoproteins in particular.

Labeling

PNGase F, a widely used deglycosylation enzyme, releases glycans from glycoproteins as glycosylamines. Various methods of labeling glycosylamines are known in the art, as exemplified by co-owned U.S. Pat. Nos. 8,124,792 and 8,445,292. If the glycosylamines are to be labeled with an amine-reactive dye, the dye labeling can be conducted without removal of the ammonium cation detergent. If labeling is to be performed using reductive amination of the reducing end of a glycan, rather than by releasing them from a glycoprotein as glycosylamines, the ammonium cation detergent is preferably first removed. Regardless of the method of labeling, the ammonium cation detergent may be removed before subjecting the labeled glycans or unlabeled glycoprotein to analytical methods, such as mass spectrometry, in which the presence of the ammonium cation detergent might be incompatible or would be a confounding factor.

Removal of the Detergents

Detergents used in deglycosylation protocols are preferably removed after labeling but before analysis of the labeled glycans, of the labeled glycosylamines, or of the glycoprotein or glycopeptide (which, following the deglycosylation step, is deglycosylated or aglycosylated), as detergents can be incompatible with some analytical instruments. Quaternary ammonium fatty acid detergents can be removed by precipitation with an acid, leaving behind in solution the now-deglycosylated or aglycosylated protein and the glycans released from the glycoprotein behind in the supernatant. The supernatant can then be removed by, for example, pipetting the supernatant away from the precipitate.

Detergents of Formula 1 or Formula 2 can be removed by a solid phase extraction called hydrophilic interaction liquid chromatography, or "HILIC." In studies conducted with an exemplar quaternary ammonium sulfate detergent, we found that HILIC was very effective at removing detergent from the deglycosylation solution. HILIC is a preferred embodiment for removal of ammonium sulfate or ammonium sulfonate detergents of Formula 1 used in some embodiments of the invention.

In some embodiments, the detergent or detergents may be removed by using other solid- or liquid-phase techniques. It is expected that persons of skill are familiar with various types of liquid-liquid techniques and solid phase extraction devices which are used in the art to remove detergents from a solution. The solid phase extraction devices usually comprise resins on a solid support, and the resins are conveniently disposed in a cartridge or column (for convenience of reference, reference to a "column" in the following discussion refers to either a column or a cartridge, unless otherwise required by context). Common solid phase extraction devices include reverse phase columns, normal phase cartridges or columns, ion exchange columns, and size exclusion columns. Typically, the cleanup columns bind the glycans, allowing the detergent to flow through and be discarded, after which the glycans are eluted from the column. The use of a solid- or liquid-phase extraction technique is particularly preferred when the ammonium cation detergent is not susceptible to acid precipitation or to ensure removal of any detergent that does not precipitate out of solution.

If one or more denaturants are used in addition to an ammonium cation detergent, they are typically also removed by using a cleanup column, such as a solid phase extraction column, and do not have to be LC or MS compatible.

Analysis of Glycans, Glycoproteins, or Both

Glycans can typically be eluted from a solid phase extraction device with water, after which they can be put in an analytical column or subjected to mass spectrometry ("MS"). Typical analytical means for analyzing labeled glycans or glycosylamines include high-pressure liquid chromatography, capillary electrophoresis, fluorescence analysis, mass spectrometry, or a combination of two or more of any of these. In some embodiments, the combination is of fluorescence analysis and mass spectrometry. Glycoproteins or glycopeptides deglycosylated during the course of releasing the glycans can themselves be analyzed, by any convenient means, for example, high-performance liquid chromatography, hydrophilic interaction chromatography, nuclear magnetic resonance, Western blotting, gel electrophoresis, fluorescence analysis, capillary electrophoresis, microfluidic separation, mass spectrometry, or a combination of two or more of any of these.

EXAMPLES

Example 1

This Example sets forth the method used to prepare an exemplar quaternary ammonium sulfate detergent, tetramethyl ammonium dodecyl sulfate.

Twenty mL of AMBER LYST® 36 (Sigma-Aldrich, St. Louis, Mo.), a cation-exchange resin, was loaded into a glass chromatography column with a coarse frit and rinsed with ten column volumes of water. Tetramethylammonium hydroxide was passed through the column as an aqueous solution, and the eluent was monitored with pH paper to determine the transition from neutral to basic pH. Excess tetramethylammonium hydroxide was rinsed from the column with water, and an aqueous solution of sodium dodecyl sulfate was loaded onto the column. The molar amount of SDS loaded was approximately tenfold less than the molar amount of tetramethylammonium ions estimated to be present on the resin. The column was flushed with water. Finally, the water was removed by rotary evaporation, yielding a white solid composed of tetramethylammonium dodecyl sulfate.

Example 2

This Example sets forth the protocol used for comparisons of the amount of glycan released from glycoproteins by enzymatic digestion following denaturing with either (a) sodium dodecyl sulfate or (b) an exemplar quaternary ammonium sulfate detergent, tetramethyl ammonium dodecyl sulfate.

Denaturation Step

A series of glycoproteins were selected for testing ranging from having one glycosylation to multiple sites. Aliquots of 40 to 100 µg solution of each glycoprotein to be tested were prepared in 20 µl of pH 7.5 in a compatible reaction buffer of choice, forming a solution containing glycoprotein and water. Two pi of a 50 mM solution of either sodium dodecyl sulfate (detergent 1) or tetramethyl ammonium dodecyl sulfate (detergent 2) were added to the glycoprotein/buffer solution for a final concentration of 4.5 mM of the detergent. The mixtures were then incubated for 3 minutes at 90° C.

Enzymatic Digestion Step

Two µl of 1 mg/ml of PNGase F in tetramethyl ammonium HEPES buffer, pH8, was added and the resulting mixture was incubated for at 37° C. for one hour.

Labeling Step

Following this incubation, glycans released by the PNGase F were labeled with InstantPC® dye (ProZyme, Inc., Hayward, Calif.) by adding 5 µl of the dye solution to each sample and incubating the samples for one minute at 50° C.

Cleanup Step

The labeled glycans were resuspended in 600 µl of 95:5 acetonitrile: formic acid and the solutions were loaded onto cleanup cartridges. The cartridges were then washed three times with 600 µl of a 95:5 acetonitrile: formic acid solution. The labeled glycans were then eluted with 100 µl of a solution of 200 mM ammonium formate, pH 7, containing 10% acetonitrile.

Analysis Step

One µl of each eluted sample was injected into high performance liquid chromatography (HPLC) equipment for analysis. The amount of glycans released from each glycoprotein when tetramethyl ammonium dodecyl sulfate was used as the detergent was considered to be "100%" release, which allowed a ready comparison to the amount of glycan released using the same assay on the same glycoprotein, but using sodium dodecyl sulfate rather than tetramethyl ammonium dodecyl sulfate as the detergent to denature the glycoprotein.

Example 3

This Example sets forth the results of the study reported in Example 2.

FIG. 1 is a table setting forth the results of studies comparing the use of tetramethyl ammonium dodecyl sulfate and sodium dodecyl sulfate (SDS) as detergents in a deglycosylation protocol on a series of nine glycoproteins and mixtures of glycoproteins. To permit ready comparison of how well each detergent served in the deglycosylation protocol, the amount of glycans released from each glycoprotein or mixture of glycoproteins in the assay in which tetramethyl ammonium dodecyl sulfate was used as the detergent was normalized to 100%, and the amount released then compared to the amount of glycan released when SDS was used as the detergent in the same deglycosylation protocol on the same glycoprotein. The studies included three mixtures of human antibodies of different antibody classes: hIgG, hIgA, and hIgM; an antibody, designated RM 8671, provided by the National Institute of Standards and Technology ("NIST") as a reference material for testing, and five glycoproteins currently approved by the Food and Drug Administration for therapeutic use. FIG. 2 presents the results of the comparative studies reported in FIG. 1 in the form of a graph, with error bars representing the results of three replicates. To allow ready comparison, the amount of glycans released from each glycoprotein or mixture by digestion following denaturing with tetramethyl ammonium lauryl sulfate was considered to be a 100% release, and that amount was then compared to the amount released from the same glycoprotein or glycoprotein mixture following denaturing with SDS.

For four out of nine of the glycoproteins or glycoprotein mixtures, denaturing with SDS resulted in the release of significantly fewer glycans than did the use of the exemplar quaternary ammonium sulfate detergent, and for the mixture of human IgGs, denaturing with SDS resulted in the release of almost 25% less glycan than did denaturing with the quarternary ammonium sulfate detergent. For a mixture of hIgM antibodies, denaturing with SDS resulted in the release of 18% less glycan than did denaturing with the quarternary ammonium sulfate detergent. For the therapeutic biologic agent ORENCIA®, denaturing with SDS resulted in the release of almost 15% less glycan than did denaturing with the quarternary ammonium sulfate detergent. For three of the nine glycoproteins or mixtures, using SDS to denature the glycoprotein resulted in roughly the same release of glycan compared with the amount released following denaturation of the same glycoprotein with the quarternary ammonium sulfate detergent. In the case of one glycoprotein, the chimeric mouse/human monoclonal antibody cetuximab, denaturing with SDS resulted in the release of more glycan than did the use of quarternary ammonium sulfate detergent, and in that case the difference was less than 10%. The results indicate that quarternary ammonium sulfate detergents provide generally better or equal results, and in many cases, surprisingly better results in deglycosylation protocols compared to SDS.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:
1. A method of denaturing a glycoprotein or glycopeptide of interest in vitro, said method comprising incubating said glycoprotein or glycopeptide in vitro with a solution comprising an effective amount of an ammonium cation sulfate or sulfonate detergent comprising (a) an aliphatic chain of 8-24 carbons, (b) a sulfate or sulfonate anion and (c) a tertiary or quaternary ammonium cation, wherein said aliphatic chain is covalently attached to said anion, for a time T to denature said glycoprotein or glycopeptide, thereby denaturing said glycoprotein or glycopeptide.
2. The method of claim 1, wherein said anion is a sulfate anion.
3. The method of claim 1, wherein said anion is a sulfonate anion.
4. The method of claim 1, wherein said chain of 8-24 carbons is saturated.
5. The method of claim 1, wherein said aliphatic chain is of 8-15 carbons.
6. The method of claim 1, wherein said aliphatic chain is of 8-13 carbons.
7. The method of claim 1, wherein said aliphatic chain is 12 carbons.
8. The method of claim 7, wherein said aliphatic chain is saturated.
9. The method of claim 1, wherein said aliphatic chain is in a ring configuration.
10. The method of claim 1, wherein said sulfate or sulfonate anion is covalently attached to said aliphatic chain by being attached to a benzyl which is attached to said aliphatic chain.
11. The method of claim 1, wherein said cation is a quaternary ammonium cation.
12. The method of claim 11, wherein said quaternary ammonium cation is selected from the group consisting of:

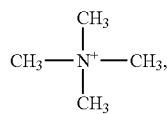
Cation 1

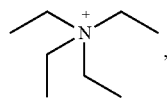
Cation 2

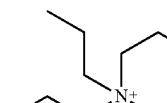
Cation 3

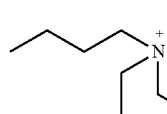
Cation 4

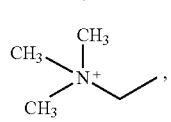
Cation 5

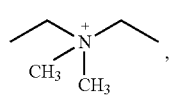
Cation 6

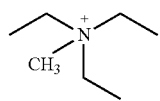
Cation 7

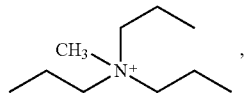
Cation 8

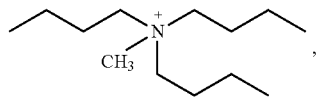
Cation 9

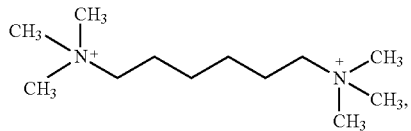
Cation 10

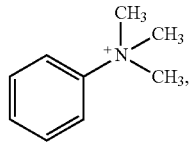
Cation 11

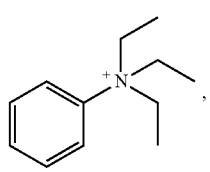
Cation 12

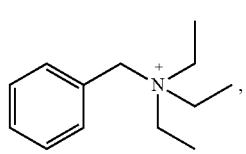
Cation 13

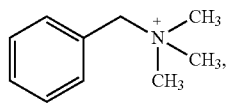
Cation 14

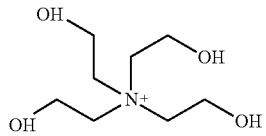
Cation 15

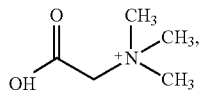
Cation 16

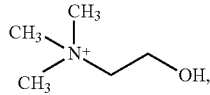
Cation 17

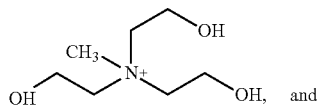
Cation 18 and

Cation 19

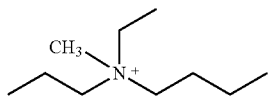

13. The method of claim 12, wherein said quaternary ammonium cation is a tetramethylammonium cation.

14. The method of claim 12, wherein said quaternary ammonium cation is a tetrabutyl, a tetraethyl, or a tetrapropyl ammonium cation.

15. The method of claim 1, wherein said ammonium cation detergent is tetra methyl dodecyl ammonium sulfate.

16. The method of claim 1, wherein said cation is a tertiary ammonium cation.

17. The method of claim 16, wherein said tertiary ammonium cation is a trimethyl, tributyl, triethyl or tripropyl ammonium cation.

18. The method of claim 1, wherein said glycoprotein or glycopeptide of interest is in a mixture of glycoproteins or glycopeptides.

19. The method of claim 1, wherein said glycoprotein or glycopeptide of interest is in a cell lysate, blood serum, blood plasma, is a fusion protein, or is a cell membrane protein.

20. The method of claim 1, further comprising the steps of heating a solution comprising said glycoprotein or glycopeptide and said ammonium cation sulfate detergent or said ammonium cation sulfonate detergent to a temperature ranging from about 80° to about 120° C., maintaining said mixture within said temperature range for time T, and then cooling said solution.

21. The method of claim 20, wherein said temperature range is from about 90° to about 100° C.

22. The method of claim 20, wherein said solution is cooled to a temperature of about 35-60° C. following said time T.

23. The method of claim 22, wherein said solution is cooled to a temperature of about 50° C.

24. The method of claim 20, further wherein said time T is between about 1 to about 10 minutes.

25. The method of claim 24, further wherein said time T is about 3 minutes.

26. The method of claim 1, further comprising releasing glycans from said denatured glycoprotein or glycopeptide by incubating said denatured glycoprotein or glycopeptide with a deglycosylation enzyme for a time sufficient to release said glycans, thereby forming a solution comprising said glycans, said glycoprotein or glycopeptide from which said glycans have been released, and said ammonium cation sulfate or sulfonate detergent.

27. The method of claim 26, further wherein either said glycoprotein or glycopeptide or said deglycosylation enzyme is immobilized on a solid support.

28. The method of claim 27, wherein said denatured glycoprotein or glycopeptide is immobilized on a solid support prior to being contacted with said deglycosylation enzyme.

29. The method of claim 26, further wherein said deglycosylation enzyme is an amidase.

30. The method of claim 29, further wherein said amidase is PNG F.

31. The method of claim 26, further wherein said released glycans are labeled following release from said glycoprotein or glycopeptide.

32. The method of claim 31, further wherein said released glycans are released as β-glycosylamines.

33. The method of claim 31, further wherein said label is fluorescent.

34. The method of claim 31, further wherein said labeled released glycans are analyzed.

35. The method of claim 34, further wherein said analysis is selected from the group consisting of high-performance liquid chromatography, hydrophilic interaction chromatography, nuclear magnetic resonance, fluorescence analysis, Western blotting, gel electrophoresis, capillary electrophoresis, microfluidic separation, and mass spectrometry or a combination of any two or more of these.

36. The method of claim 34, wherein said analyzing is by detecting a fluorescent signal from said labeled released glycans.

37. The method of claim 26, further comprising analyzing said denatured glycoprotein (now deglycosylated) or glycopeptide from which said glycans have been released.

38. The method of claim 37, further wherein said analyzing of said glycoprotein or glycopeptide from which glycans have been released is by high-performance liquid chromatography, hydrophilic interaction chromatography, nuclear magnetic resonance, Western blotting, gel electrophoresis, fluorescence analysis, capillary electrophoresis, microfluidic separation, mass spectrometry, or a combination of two or more of any of these.

39. The method of claim 37, wherein said analysis is by mass spectrometry.

40. The method of claim 1, further wherein said solution comprises a reductant, an alkylant, an additional organic solvent denaturant, a chaotrope, or a combination of any of these.

41. The method of claim 34, further wherein said ammonium cation sulfate detergent or said ammonium cation sulfonate detergent is removed prior to said analyzing.

42. The method of claim 41, wherein said removing of said ammonium cation sulfate detergent or said ammonium cation sulfonate detergent comprises flowing said solution comprising said released glycans, said glycoprotein or said glycopeptide from which said glycans have been released and said detergent into a solid phase extraction device to remove said detergent from said solution.

43. A method of denaturing a glycoprotein or glycopeptide of interest in vitro, said method comprising incubating said glycoprotein or glycopeptide in vitro with a solution comprising effective amounts of
(a) a compound of the formula:

R—Y⁻.M⁺, in which:

R is a saturated or unsaturated straight chain aliphatic group with 8-13 carbon atoms;
Y⁻ is a sulfate or sulfonate anion;
M⁺ is a cation of an element in periodic table group 1; and,
the dot indicates that the cation is ionically, not covalently, associated with the Y⁻ anion, and either
(b) an ammonium cation detergent comprising: (i) an aliphatic chain of 8-24 carbons, (ii) a carboxylate anion covalently attached to said aliphatic chain and, (iii) a tertiary or quaternary ammonium cation ionically, not covalently, associated with the carboxylate anion, or
(b') a molar excess of quaternary ammonium cations, or of tertiary ammonium cations, or of both.

44. A method of claim 43, wherein said R is an aliphatic group having 12 carbons.

45. A method of claim 43, wherein said Y⁻ is a sulfate anion.

46. A method of claim 43, wherein said tertiary or quaternary ammonium cation of said ammonium cation detergent is a quaternary ammonium cation.

47. A method of claim 43, wherein said ammonium cation detergent is tetramethylammonium acetate or tetramethylammonium laurate.

48. The method of claim 43, wherein said molar excess of said quaternary ammonium cations or tertiary ammonium cations is of quaternary ammonium cations.

49. The method of claim 46, wherein said quaternary ammonium cation is selected from the group consisting of:

Cation 1
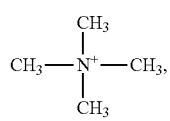

Cation 2
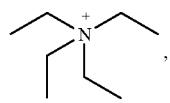

Cation 3
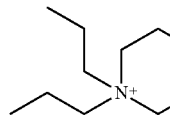

Cation 4
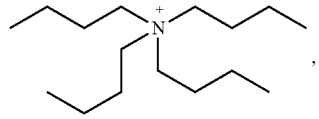

Cation 5
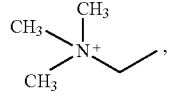

Cation 6
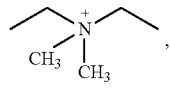

Cation 7
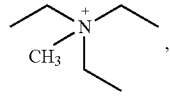

Cation 8
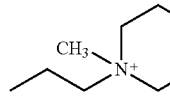

Cation 9
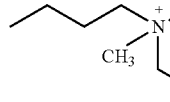

-continued

Cation 10
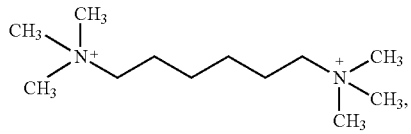

Cation 11
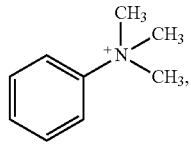

Cation 12
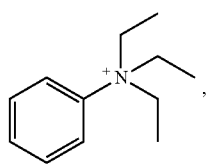

Cation 13
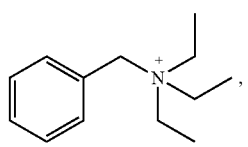

Cation 14
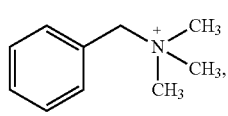

Cation 15
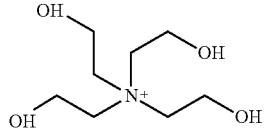

Cation 16
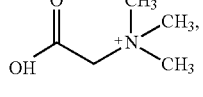

Cation 17
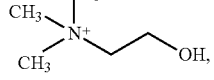

Cation 18
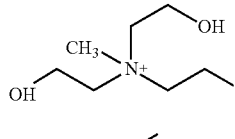

and

Cation 19
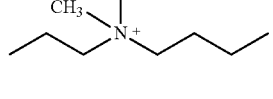

50. The method of claim 46, wherein said quaternary ammonium cation is tetramethyl ammonium.

* * * * *